United States Patent
Ngo et al.

(10) Patent No.: US 9,662,231 B2
(45) Date of Patent: May 30, 2017

(54) POLYMER SCAFFOLDS HAVING ENHANCED AXIAL FATIGUE PROPERTIES

(71) Applicant: Abbott Cardiovascular Systems Inc., Santa Clara, CA (US)

(72) Inventors: Michael Huy Ngo, San Jose, CA (US); Samit Mustafa, Sunnyvale, CA (US); Syed Hossainy, Hayward, CA (US); Mikael Trollsas, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 388 days.

(21) Appl. No.: 13/840,257

(22) Filed: Mar. 15, 2013

(65) Prior Publication Data

US 2014/0277372 A1    Sep. 18, 2014

(51) Int. Cl.
| | |
|---|---|
| A61F 2/82 | (2013.01) |
| A61F 2/915 | (2013.01) |
| B29C 55/26 | (2006.01) |
| B29C 49/08 | (2006.01) |
| B29L 31/00 | (2006.01) |

(52) U.S. Cl.
CPC ............ *A61F 2/82* (2013.01); *A61F 2/915* (2013.01); *B29C 55/26* (2013.01); *A61F 2002/91575* (2013.01); *B29C 49/08* (2013.01); *B29C 2793/0009* (2013.01); *B29L 2031/753* (2013.01); *B29L 2031/7542* (2013.01); *Y10T 29/49863* (2015.01)

(58) Field of Classification Search
CPC .. A61F 2/82; A61F 2/915; A61F 2/958; A61F 2/2412; A61F 2/86; A61F 2/95; A61F 2/954; A61F 2002/91575; B29C 55/26; B29C 2793/0009; B29C 49/08; B29L 2031/7542; B29L 2031/753; Y10T 29/49863

See application file for complete search history.

(56) References Cited

U.S. PATENT DOCUMENTS

| | | | |
|---|---|---|---|
| 6,066,167 A | 5/2000 | Lau et al. | |
| 7,964,136 B2 | 6/2011 | Sabaria | |
| 8,414,528 B2 | 4/2013 | Liu et al. | |
| 2006/0076708 A1 | 4/2006 | Huang et al. | |

(Continued)

FOREIGN PATENT DOCUMENTS

WO     WO 2007/105068     9/2007

OTHER PUBLICATIONS

Bosiers et al., "Coronary and endovascular applications of the Absorb™ bioresorbable vascular scaffold", Interv. Cardiol. 4(6), pp. 621-631 (2012).

(Continued)

*Primary Examiner* — David Bryant
*Assistant Examiner* — Jun Yoo
(74) *Attorney, Agent, or Firm* — Squire Patton Boggs (US) LLP

(57) ABSTRACT

A medical device includes a polymer scaffold crimped to a catheter having an expansion balloon. The scaffold has a morphology resulting from a biaxially expanded tube arranged to provide a more balanced, or less anisotropic axial and radial mechanical properties. The scaffold has improved mechanical properties suited for use as a balloon expandable scaffold implanted in a peripheral vessel of the body.

19 Claims, 12 Drawing Sheets

(56) References Cited

U.S. PATENT DOCUMENTS

| | | |
|---|---|---|
| 2007/0073384 A1 | 3/2007 | Brown et al. |
| 2009/0105800 A1 | 4/2009 | Sabaria |
| 2009/0163989 A1 | 6/2009 | Contiliano et al. |
| 2010/0004735 A1 | 1/2010 | Yang et al. |
| 2011/0062638 A1 | 3/2011 | Glauser et al. |
| 2011/0066222 A1 | 3/2011 | Wang et al. |
| 2011/0190871 A1 | 8/2011 | Trollsas et al. |
| 2011/0190872 A1 | 8/2011 | Anukhin et al. |
| 2012/0059451 A1 | 3/2012 | Zhang et al. |
| 2012/0073733 A1 | 3/2012 | Ngo et al. |
| 2013/0025110 A1 | 1/2013 | Stankus et al. |
| 2013/0041129 A1 | 2/2013 | Steichen et al. |
| 2014/0025161 A1 | 1/2014 | Stankus et al. |
| 2014/0039604 A1* | 2/2014 | Trollsas et al. .............. 623/1.15 |
| 2014/0114399 A1* | 4/2014 | Hossainy ............. B29C 69/001 623/1.16 |

OTHER PUBLICATIONS

Duerig et al., "Overview of Superelastic Stent Design", Min. Invas. Ther & Allied Technol. 9, pp. 235-246 (2000).

\* cited by examiner

| Attribute | FIG.10A | | | | v80 |
|---|---|---|---|---|---|
| | item | in | mm | other | Comments |
| Total Length | — | 0.00 | | | Nominal for 40mm balloon, no Marker |
| Number of Rings | — | | | 17 | |
| Number of Links per Ring | — | | | 2 | Evenly distributed |
| Number of Crests per Ring | — | | | 12 | Internal Pattern: U U W U U Y U U W U U Y |
| Cut Tube OD | — | 0.276 | 7 | | |
| Wall Thickness | — | 0.011 | 0.279 | | |
| Strut Width | 363 | 0.008 | 0.200 | | |
| | | | | | |
| Link Width | 363 | 0.008 | 0.200 | | |
| Strut Length | 364 | 0.047 | 1.200 | | |
| Proximal Strut Length | | 0.052 | 1.322 | | Designed for same theoretical max expansion as body |
| Angle (U) - deg | 368 | | | 81 | Angles based on 7mm tube |
| Angle (W) - deg | 367 | | | 81 | Angles based on 7mm tube |
| Angle (Y) - deg | 366 | | | 81 | Angles based on 7mm tube |
| | | | | 66 | |
| | | | | 66 | |
| Inner Radius (U) | 372 | 0.007 | 0.18 | | |
| Outer Radius (U) | 372 | 0.015 | 0.38 | | |
| Inner Radius (W) | 372 | 0.007 | 0.18 | | |
| Outer Radius (W) | 372 | 0.015 | 0.38 | | |
| Inner Radius (Y) | 372 | 0.007 | 0.18 | | |
| Outer Radius (Y) | 372 | 0.015 | 0.38 | | |

FIG. 11A

| Attribute | FIG.10B | v79 | | |
|---|---|---|---|---|
| | item | in | mm | other |
| Total Length | — | 1.48 | 37.7 | |
| Number of Rings | — | | | 17 |
| Number of Links per Ring | — | | | 2 |
| Number of Crests per Ring | — | | | 8 |
| Cut Tube OD | — | 0.28 | 7 | |
| Wall Thickness | — | 0.011 | 0.279 | |
| Strut Width | 263a | 0.012 | 0.300 | |
| | | | | |
| Link Width | 263b | 0.008 | 0.300 | |
| Strut Length | 264 | 0.069 | 1.740 | |
| | | | | |
| Angle (U) - deg | 268 | | | 81 |
| Angle (W) - deg | 267 | | | 81 |
| Angle (Y) - deg | 266 | | | 81 |
| | | | | |
| Inner Radius (U) | 272 | 0.0071 | 0.18 | |
| Outer Radius (U) | 273 | 0.019 | 0.48 | |
| Inner Radius (W) | 272 | 0.0071 | 0.18 | |
| Outer Radius (W) | 273 | 0.019 | 0.48 | |
| Inner Radius (Y) | 272 | 0.0071 | 0.18 | |

FIG. 11B

POLYMER SCAFFOLDS HAVING ENHANCED AXIAL FATIGUE PROPERTIES

FIELD OF THE INVENTION

The present invention relates to drug-eluting medical devices; more particularly, this invention relates to polymeric scaffolds that are expanded by a delivery balloon.

BACKGROUND OF THE INVENTION

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Even before the radial yield strength is exceeded there may be permanent deformation in the stent a following radial compressive load, but this degree of permanent deformation somewhere in the stent is not severe enough to have a significant effect on the stent's overall ability to radially support a vessel. Therefore, in some cases the art may view "radial yield strength" as the maximum radial loading, beyond which the scaffold stiffness changes dramatically. "Radial yield strength" units are sometimes force-divided-by-length, which is an expression of radial yield strength on a per-unit-length basis. Thus, for a radial yield strength per unit length, e.g., F N/mm, the radial load which, if it exceeds this value, would result in significant change in stiffness for a stent having two different lengths, L1 and L2, would therefore be the product F*L1 and F*L2, respectively. The value F, however, is the same in both cases, so that a convenient expression can be used to appreciate the radial yield strength independent of the length of the stent. Typically, the radial force that identifies the point where stiffness is lost does not change much on a per-unit-length basis when the stent length changes.

A commonly used type of peripheral stent is the self-expanding stent made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. Complications resulting from COF are discussed in Schwartz, Lewis B. et al. *Does Stent Placement have a learning curve: what mistakes do we as operators have to make and how can they be avoided?*, Abbott Laboratories; Abbott Park, Ill., USA. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF. Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel.

A balloon-expanded polymer scaffold, such as that described in US 2010/0004735 is made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The polymer scaffold described in US 2010/0004735, as opposed to a metal stent, is intended to remain in the body for only a limited period of time. The scaffold is made from a biodegradable or bioerodable polymer. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a polymer scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLDLA") with less than 10% D-lactide, and PLLA/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bioabsorbable polymer such as PLLA or PLGA.

Various studies have been conducted on processing steps for making tubes for polymer scaffolds intended for implantation within a coronary artery, i.e., a coronary scaffold. See US 2011/0062638. These studies have examined such properties as radial strength, radial stiffness, ultimate strain, fracturing of scaffolds that are radially expanded and homogeneity of properties across a wall thickness. Included amongst these studies are reports on how mechanical properties are affected by varying the degree of axial expansion and radial expansion, in different combinations of ratios (Table 1 of US 2011/0062638). For coronary scaffolds a radial expansion of about 400% and axial expansion of about 20% of an extruded polymer tube has been used. This biaxially expanded tube is cut into the coronary scaffold using a laser.

Stents implanted in coronary arteries are primarily subjected to radial loads, typically cyclic in nature, which are due to the periodic contraction and expansion of vessels as blood is pumped to and from a beating heart. Stents implanted in peripheral blood vessels, or blood vessels outside the coronary arteries, e.g., iliac, femoral, popliteal, renal and subclavian arteries, however, must be capable of sustaining both radial forces and crushing or pinching loads. These stent types are implanted in vessels that are closer to the surface of the body. Because these stents are close to the surface of the body, they are particularly vulnerable to crushing or pinching loads, which can partially or completely collapse the stent and thereby block fluid flow in the vessel.

As compared to a coronary scaffold, which is designed to counteract primarily radial loads, a peripheral scaffold must take into account the significant differences between pinching or crushing loads and radial loads, which is discussed for metal stents in Duerig, Tolomeo, Wholey, Overview of superelastic stent Design, Min Invas Ther & Allied Technol 9(3/4), pp. 235-246 (2000) and Stoeckel, Pelton, Duerig, *Self-Expanding Nitinol Stents—Material and Design Considerations*, European Radiology (2003). The corresponding crushing and radial stiffness properties of the stent also can vary dramatically. As such, a stent that possesses a certain degree of radial stiffness does not, generally speaking, also indicate the degree of pinching stiffness possessed by the stent. The two stiffness properties are not the same, or even similar.

In addition to crushing loads, scaffolds intended for peripheral vessels, as opposed to coronary scaffolds, experience a quite different time-varying loading, to such an extent that the traditional measure of a stent's fitness for use, i.e., its radial strength/stiffness, is not an accurate measure of whether the peripherally implanted scaffold ("peripheral scaffold") possesses the time-dependent mechanical properties for providing support within the peripheral vessel for the duration needed. This is because a peripheral scaffold is placed in a significantly different environment from a coronary scaffold. The vessel size is larger. And there is much more movement of the vessel, especially when located close to an appendage. As such, a scaffold intended for a peripheral vessel will need to be able to sustain more complex loading, including a combination of axial, bending, torsional and radial loading. See e.g. Bosiers, M. and Schwartz, L., *Development of Bioresorbable Scaffolds for the Superficial Femoral Artery*, SFA: CONTEMPORARY ENDOVASCULAR MANAGEMENT (Interventions in the SFA" section). These and related challenges facing peripherally implanted stents and scaffolds are also discussed in US2011/0190872. IN particular, it has been found that axial loading associated with walking is a key contributor to fracturing of scaffold struts.

There is a need to develop a prosthesis for treating peripheral blood vessels that can maintain its structural integrity for a period of time long enough to provide a mechanical support for the vessel, until this support is no longer needed. There is a further need to develop such a prosthesis that has a controlled or reduced amount of recoil and that can provide the desired axial and radial strength and toughness needed for areas where there is a high degree of vascular motion.

SUMMARY OF THE INVENTION

In response to these needs there is provided a peripherally-implantable and bio-erodible polymer scaffold formed from a biaxially-expanded tube having mechanical properties better suited to meet demands imposed on a peripherally-implanted scaffold. By forming the peripheral scaffold having a combined balanced, isotropic, or less anisotropic biaxially-expanded tube and relatively high degree of total strain (during the biaxial expansion), it is found that the scaffold is more capable of providing the structural support and maintaining its structural integrity within the vessel.

Tubes formed into coronary scaffolds have been made according to an expansion process having 400% radial and 20% axial expansion, which produces a tube having a very anisotropic orientation with regard to the axial verses radial loading directions, i.e., the tube material has predominantly a circumferential polymer orientation. For a peripheral vessel it has been found through tests that a scaffold with a more balanced biaxial polymer orientation can improve fatigue fracture resistance. Indeed it was discovered that the axial fatigue fracture resistance was improved using tubes with a more biaxial polymer orientation (expansion ratios 400/200). It was further discovered that the elongation at break varies dramatically in the axial and circumferential orientation for tubes produced with the current expansion process (400/45) once the anisotropic tube material had been exposed to water for more than 2 hours, whereas there is little difference seen for the dry materials. Also, no difference was observed for an elongation at break between axial and circumferential directions for tubes with a more balanced or even biaxial polymer orientation (e.g., an expansion ratio 2, 1 or between 2-1) after exposure to water (37° C.) for at least 6 days.

Tests comparing the control (400% radial and 45% axial) to 400% and 200% showed the latter lost some radial strength/stiffness due to it being more strained in the axial direction. By being more fracture resistant in the axial direction, there is some loss of mechanical strength in the radial direction. However, the drop was not significant. In addition, the 400% radial and 200% axial expansion improved the scaffold recoil after 1 hour and the scaffold rapidly reached recoil levels after 24 hour that were improved as compared to the control group.

According to one aspect of the invention, from results observed by axial fatigue testing, radial strength, and recoil it is suggested that a biaxial less anisotropic tube material would produce the better scaffold for a peripheral vessel. A preferred expansion ratio is about 2, which generates an elongation ratio (circumferential/axial) after soaking for 6 days at 37° C. of about 1 or less than 1.

According to one aspect of the invention, there is a balloon-expandable scaffold forming ring structures. The scaffold is formed from a balanced, biaxially expanded tube where the ratio of radial to axial expansion is about 2 or less than 2. Each ring is connected to adjacent rings by no more than two links and each ring has at least 8 crests or 12 crests formed by strut elements.

According to a first aspect of invention there is a balloon expanded, peripherally implanted scaffold, method of making such a scaffold, or a scaffold crimped to a balloon, the scaffold having a biaxial expansion, total strain, and/or ratio of radial to axial elongation at break producing improved toughness in the axial direction without significantly adversely affecting other mechanical properties. The scaffold attains at least 80%, or at least 90% of the pre-crimp diameter after being crushed to 70% of the pre-crimp diameter.

According to a second aspect of invention there is a balloon expanded, peripherally implanted scaffold or method of making such a scaffold, or a scaffold crimped to a balloon, the scaffold having a biaxial expansion, total strain, and/or ratio of radial to axial elongation at break providing improved recoil characteristics during an acute period, one hour from implant, 1 day, and one week form implant.

According to a third aspect of invention there is a balloon expanded, peripherally implanted scaffold, method of making such a scaffold, or a scaffold crimped to a balloon, the scaffold having a biaxial expansion, total strain, and/or ratio of radial to axial elongation at break and the scaffold having at most two links and 8 or 12 crests for a ring.

According to a fourth aspect of invention there is a balloon expanded, peripherally implanted scaffold, a method of making such a scaffold, or a scaffold crimped to a balloon, the scaffold having a biaxial expansion, total strain, and/or ratio of radial to axial elongation at break, and the scaffold having a pre-crimp diameter, or being made from a tube diameter greater than 5 mm, or about 1.1, 1.0, 1.2, 1.3, 1.4, 1.5 or about 1.0-1.5 times greater than an expanded diameter or post-dilation diameter; an expanded diameter or pre-crimp diameter that is about 2, 2.5, 3, or 3.5 times greater than a crimped diameter; and/or an OD of 7 mm and/or wall thickness of 0.279 mm.

According to a fifth aspect of invention there is a balloon expanded, peripherally implanted scaffold, a method of making such a scaffold, or a scaffold crimped to a balloon, the scaffold having a biaxial expansion, total strain, and/or ratio of radial to axial elongation at break producing a recoil amount of 10%, and a post-dilation diameter that is more than 90% of an expanded diameter.

For each of the first, second, third, fourth and fifth aspects of invention the biaxial expansion may range from about 400-500 in the radial direction and from about 150-200 in the axial direction; the ratio RE/AE may be between about 2 and 1, 2.5 to 1, 3 to 1, and 4 to 1.

For each of the first, second, third, fourth and fifth aspects of invention pertaining to a biaxially expanded tube, scaffold or scaffold crimped to a balloon the morphology of the scaffold/tube material in axial and radial directions comprises a preferred orientation of polymer crystals resulting from a ratio of radial to axial expansion of about 2, less than 2, less than 1 or between 2-1; and/or the material has a ratio of radial to axial elongation at break of about 1 or less than 1.

According to another aspect of the invention, there is provided a scaffold formed from a balanced biaxially expanded tube, having at most two links connecting adjacent ring structure and with or without an increased number of crests to extend the scaffold's fatigue life during the period of time when the scaffold is needed to provide mechanical support to the vessel, e.g., during the first about one, two or three months following implantation. Tests have revealed that for a peripherally-implanted scaffold, particularly for scaffold located within arteries of appendages, failure in the scaffold structure has most often occurred due to repeated axial compression/extension and bending. Although the scaffold is in general subjected to a complex and time-varying combination of radial, axial, bending and torsion loads, it has been found that prior scaffold designs have been mostly susceptible to crack formation due to repeated cyclic axial and bending loads, e.g., 500,000 cycles of 7% axial compression/extension, which is considered equivalent to walking over a six month period. Repeated impacts between ring structures, longitudinal buckling (bending) of links or other behavior that may result from a reduction of axial and bending stiffness have been found to have a significant negative impact on vessel support or scaffold integrity based on in-vivo studies.

According to another embodiment, a peripherally-implanted medical device includes a balloon-expanded scaffold formed from a radially expanded polymer tube, the scaffold forming a network of rings interconnected by links, including at least 8 or 12 crests per ring, and at most 2 links connecting substantially all pairs of adjacent rings, wherein for any ring of the scaffold there are an equal number of unsupported crowns on each side of each crown connected to a link. The two links allows the structure to better absorb/distribute stresses induced during combined axial loading and bending. Moreover, it was found that the structure's overall fatigue life is significantly increased when two links are used. Additionally, symmetry of crowns about a link helps to more equally distribute stresses, or reduce stress concentrations near crowns to improve fatigue life during axial loading and bending.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 11A and 11B are tables showing examples of scaffold features in accordance with aspects of the disclosure.

DETAILED DESCRIPTION OF EMBODIMENTS

Figure 1:
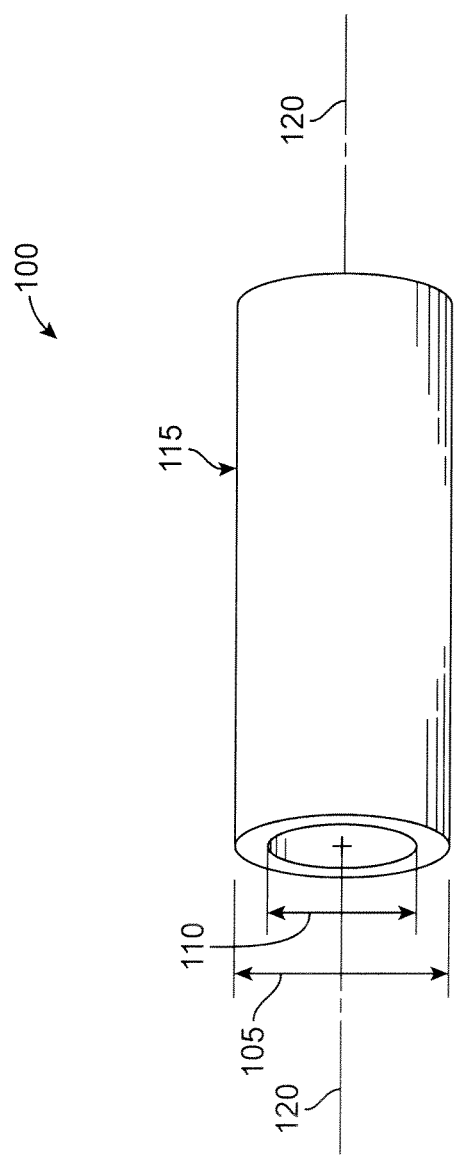
FIG. 1 is a perspective view of a deformed polymer tube. The tube is formed into a scaffold.

The disclosure proceeds as follows. First, definitions of terms that may be used during the course of the subsequent disclosure are explained. Embodiments of processes for forming a deformed polymer tube from a precursor are provided. According to the disclosure, the crush recoverable and balloon expandable scaffold is cut from a tube (FIG. 1) formed through a process intended to enhance mechanical properties of the scaffold including fracture toughness. A discussion of this process, followed by a discussion of a study conducted to determine a best or improved biaxial expansion for a tube made into a scaffold. Finally, two preferred scaffold designs are disclosed.

For purposes of this disclosure, the following terms and definitions apply:

The term "about" means 10%, 5%, or 2% less or more than a stated value, or a one-sigma variation from a stated mean value.

"Reference vessel diameter" (RVD) is the diameter of a vessel in areas adjacent to a diseased section of a vessel that appear either normal or only minimally diseased.

"Minimal lumen diameter" (MLD) is the diameter of a diseased section of a vessel at the site of maximal reduction in the diameter.

% "Diameter restenosis" (% DS) is the percent difference between the reference vessel diameter and the minimal lumen diameter: (RVD−MLD)/RVD "Acute gain" is defined as the difference between pre- and post-procedural minimal lumen diameter.

"Late loss" is defined as the difference between minimal luminal diameter after the procedure or post-percutaneous coronary intervention (PCI) and minimal luminal diameter at follow-up.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "pre-crimp diameter" means an OD of a tube, or the scaffold before it is crimped to a balloon. Similarly, a "crimped diameter" means the OD of the scaffold when crimped to a balloon. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter.

"Recoil" means the response of a material following the plastic/inelastic deformation of the material. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

The glass transition temperature (referred to herein as "Tg") is the temperature at which the amorphous domains of a polymer change from a brittle vitreous state to a solid deformable or ductile state at atmospheric pressure. In other words, Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility of polymer chains. A lower end of Tg is Tg-LOW, a midpoint is Tg-MID and upper end is Tg-HIGH.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e radial strength.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. As noted earlier, a scaffold or stent having a desired radial force can have an unacceptable crush recovery. And a scaffold or stent having a desired crush recovery can have an unacceptable radial force. Crush recovery and crush resistance aspects of scaffolds is described in greater detail in US20110190871.

The term "morphology" refers to the microstructure of the polymer which maybe characterized, at least in part, by the percent crystallinity of the polymer, the relative size of crystals in the polymer, the degree of uniformity in spatial distribution of crystals in the polymer, and the degree of long range order or preferred orientation of molecules and/or crystals. Morphology may also refer to the degree of phase separation in a rubber-toughened material. The crystallinity percentage refers to the proportion of crystalline regions to amorphous regions in the polymer. Polymer crystals can vary in size and are sometimes geometrically arranged around a nucleus, and such arrangement may be with or without a preferred directional orientation. A polymer crystal may grow outwardly from the nucleus as additional polymer molecules join the ordered arrangement of polymer molecule chains. Such growth may occur along a preferred directional orientation.

The degree of biaxial expansion of an original tube, or precursor, into an expanded tube (FIG. 1), which is formed into a balloon-expanded scaffold, is expressed in terms of a radial expansion (RE) and an axial expansion (AE):

$$RE \% = [(\text{expanded tube inner diameter})/(\text{precursor inner diameter}) - 1] \times 100$$

$$AE \% = [(\text{expanded tube length})/(\text{precursor tube length}) - 1] \times 100.$$

Figure 12A:
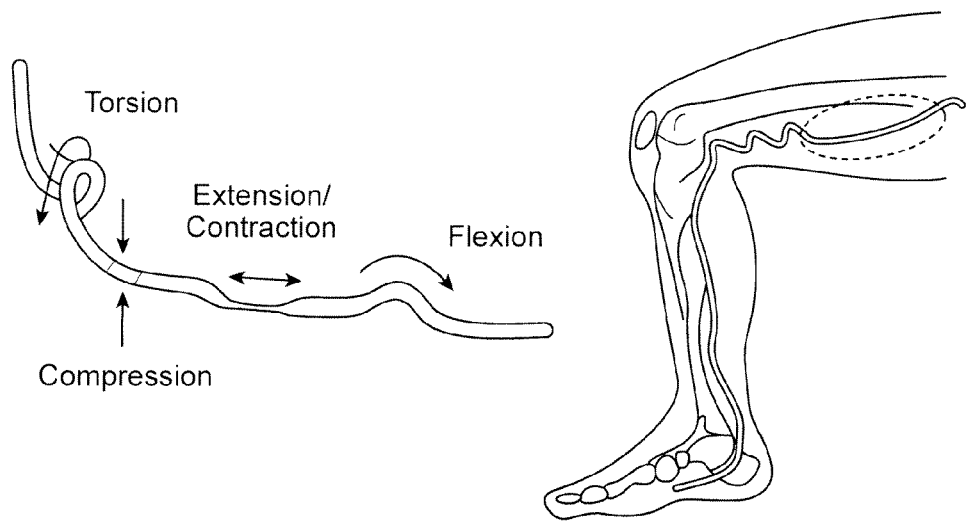
FIGS. 12A and 12B are figures showing the complex loading environment on a scaffold implanted within the superficial femoral artery of the leg.
Figure 12B:
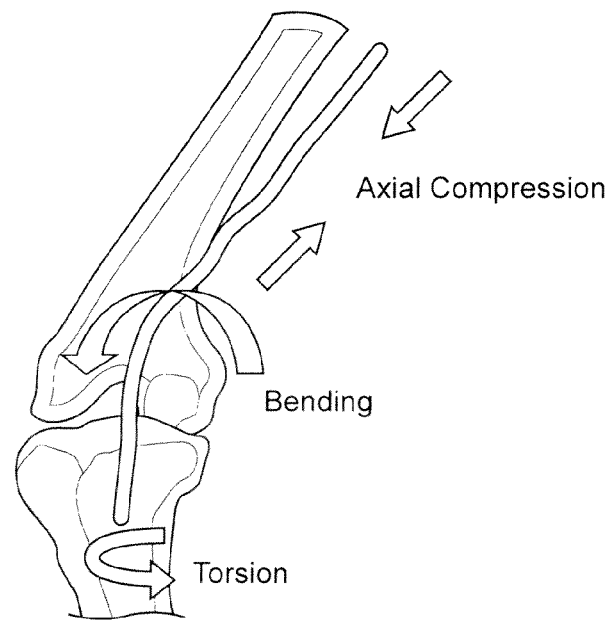

The femoral artery provides a dynamic environment for vascular implants as various forces may crush, twist, extend, or shorten the device simultaneously. FIGS. 12A-12B illustrate the nature of these forces acting on the femoral artery of the leg. The force application may vary between point load to distributed load or a combination thereof and also as a function of time. Recent results have shown that bioresorbable scaffolds made from highly crystalline PLLA can provide crush recovery without causing a permanent and constant outward radial force on the vessel. The permanent and constant outward radial force may be the cause of late clinical issues with nitinol self-expandable stents. However, a remaining challenge with bioresorbable scaffolds is to make them optimally fracture resistant as a function of time; that is, to improve their fatigue life or survivability under a variety of dynamic loading environments.

The fracture resistance of a vascular scaffold depends not only on the design and the material, but is also the manufacturing process and deployment parameters. Therefore it is in particular necessary to have a process, design, and a delivery system that allows the scaffold to be uniformly expanded and deployed. As a consequence of non-uniform deployment the various struts and crowns of a scaffold will potentially be exposed to very different forces and motions, which has a deleterious effect on the fatigue life.

Figure 7:
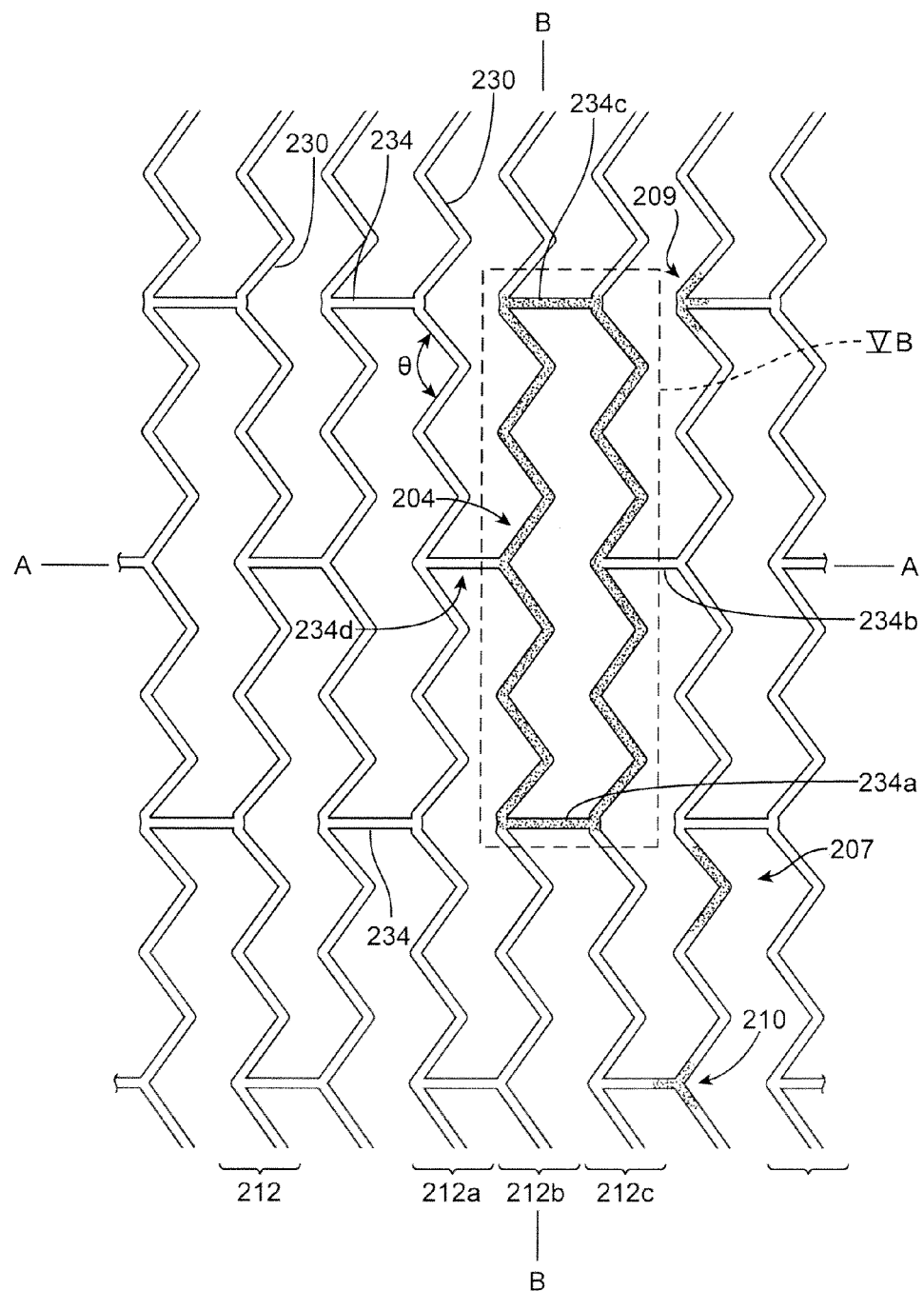
FIG. 7 is a partial planar view of a scaffold pattern according to a first embodiment of a scaffold.
Figure 9:
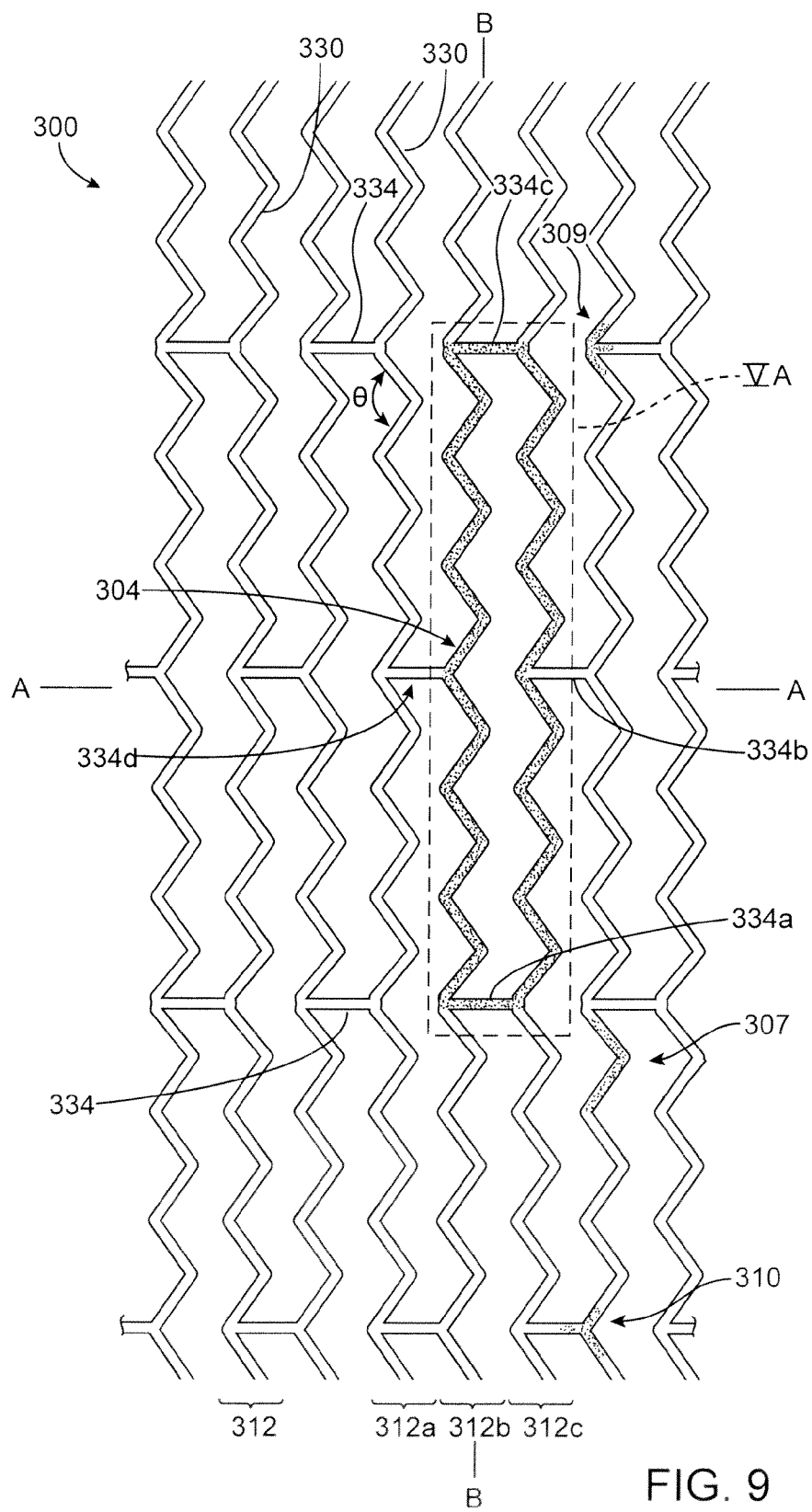
FIG. 9 is a partial planar view of a scaffold pattern according to a second embodiment of a scaffold.

The polymer scaffold illustrated in FIGS. 7 and 9 are formed from a poly(L-lactide) ("PLLA") tube 101 as depicted in FIG. 1. The process for forming tube 101 begins with extrusion of a tube precursor. Raw PLLA resin material heated above the melt temperature of the polymer is then extruded through a die at a preferred extrusion temperature of 450 Deg. Fahrenheit. Further details of this step of the process are described in US 2011/0066222 (hereinafter the '222 publ.). A carefully controlled radial and axial expansion of the formed precursor, preferably using a form of blow-molding, follows. This expansion process is employed to produce desired mechanical properties of the scaffold, starting with the precursor. The desirable properties include dimensional and morphological uniformity, e.g., crystallinity, wall thickness and "roundness", yield strength, stiffness and fracture toughness. The resulting tube 101 is then formed into a scaffold using a laser cutting process.

Expansion of the precursor is undertaken using carefully controlled parameters including pressure, rate and temperature during the expansion of the precursor. Expansion preferably occurs in both the axial and radial direction by prescribed amounts to achieve desired results. The PLLA precursor is heated above the PLLA glass transition temperature (i.e., 60-70 degrees C.) but below the melt temperature (165-175 degrees C.), preferably, around 110-120 degrees C.

The preferred blow molding process deforms the precursor progressively at a predetermined longitudinal speed along the longitudinal axis of the precursor. The tube deformation process is intended to orient polymer chains in radial and/or biaxial directions, as described in greater detail below. As mentioned above, the orientation or deformation causing re-alignment is performed according to a precise selection of processing parameters, e.g. pressure, heat (i.e., temperature), deformation rate, to affect material crystallinity and type of crystalline formation during the deformation process.

In an alternative embodiment the tube may be made of poly(L-lactide-co-glycolide), poly(D-lactide-co-glycolide) ("PLGA"), polycaprolactone, ("PCL"), and other suitable semi-crystalline copolymers or blends of these polymers. Rubber toughen material could also be achieved by using block copolymers or polymer blends of the above materials in combination with low Tg materials such as polycaprolactone, polyethyleneglycol and polydioxanone. Alternatively multilayered structures could be extruded. Material choices may be limited when taking into account the complex loading environment associated with many peripheral vessel locations, particularly those located close to limbs.

Blow molding includes first positioning the tube precursor (or precursor) in a hollow cylindrical member or mold. The mold controls the degree of radial deformation of the precursor by limiting the deformation of the outside diameter or surface of the precursor to the inside diameter of the mold. While in the mold, the precursor temperature is above Tg of PLLA to facilitate deformation. This temperature is a processing parameter referred to as the "expansion temperature" or "process temperature." The heating to the expansion temperature can be achieved by heating a gas to the expansion temperature and discharging the heated gas onto an exterior surface of the mold containing the precursor.

While in the mold, one end of the precursor is sealed or blocked. Thus, introduction of gas into the opposite end of the precursor will increase internal fluid pressure relative to ambient pressure in a region between the outer surface of the precursor and the inner surface of the mold. The internal fluid pressure is a processing parameter referred to as the "expansion pressure" or "process pressure." Examples of gas that may be used to create the expansion pressure include without limitation ambient air, substantially pure oxygen, substantially pure nitrogen, and other substantially pure inert gases. In combination with other blow molding process parameters, the expansion pressure affects the rate at which the precursor deforms radially and axially to produce the tube 101 shown in FIG. 1. Blow molding may include pulling one end of the precursor. A tensile force, which is another processing parameter, is applied to one end of the precursor while holding the other end of the precursor stationary. The radially and axially deformed precursor may then be cooled from above Tg to below Tg, either before or after decreasing the pressure and/or decreasing tension. Cooling at a controlled temperature, or rate of temperature drop, helps insure the tube 101 maintains the proper shape, size, and length following radial expansion and axial extension. Slow cooling through a temperature range between Tm and Tg might result in a loss of amorphous chain orientation and cause a decrease in fracture toughness of the finished scaffold. Preferably, though not necessarily, the deformed precursor can be cooled quickly or quenched in relatively cold gas or liquid to a temperature below Tg to maintain chain orientation that was formed during tubing expansion. The deformed precursor after cooling produces the tube 101, which may be then cut to produce the scaffold described in FIGS. 4 and 7. FIGS. 2A-2D of US2012/0073733 schematically depict a molding system 500 for simultaneous radial and axial deformation of a polymer tube.

Quiescent crystallization can occur from a polymer melt, which is to be distinguished from crystallization that occurs solely due to polymer deformation. In general, quiescent crystallization tends to occur in a semi-crystalline polymer at temperatures between Tg and Tm of the polymer. The rate of quiescent crystallization in this range varies with temperature. Near Tg, nucleation rate is relatively high and quiescent crystal growth rate is relatively low; thus, the polymer will tend to form small crystals at these temperatures. Near Tm, nucleation rate is relatively low and quiescent crystal growth rate is relatively high; thus, the polymer will form large crystals at these temperatures.

As previously indicated, crystallization also occurs due to deformation of the polymer. Deformation stretches long polymer chains and sometimes results in fibrous crystals generally oriented in a particular direction. Deforming a polymer tube made of PLLA by blow molding at a particular expansion temperature above Tg results in a combination of deformation-induced crystallization and temperature-induce crystallization.

As indicated above, the ability of the polymer to deform is dependent on the blow molding temperature ("expansion temperature") as well as being dependent on the applied internal pressure ("expansion pressure") and tensile force. As temperature increases above Tg molecular orientation is more easily induced with applied stress. Also, as temperature approaches Tm, quiescent crystal growth rate increases and quiescent nucleation rate decreases. Thus, it will also be appreciated that the above described blow molding process involves complex interaction of the processing parameters all of which simultaneously affect crystallinity percentage, crystal size, uniformity of crystal distribution, and preferred molecular or crystal orientation. As mentioned earlier, in a preferred embodiment the PLLA tube was made entirely of PLLA. The preferred levels are given below for the blow molding process parameters for a PLLA precursor having an initial (before blow molding) crystallinity percentage of up to about 20% and more narrowly from about 5% to about 15%. Applicants believe the blow molding process parameter levels given below result in a deformed PLLA tube having a crystallinity percentage below 50% and more narrowly from about 30% to about 40%. After expansion, the tube 101 may be subjected to an extended period of elevated temperature. In one embodiment, a PLLA tube 101 is subjected to a temperature of between about 40-50 Deg Celsius or about 47 Deg Celsius before laser-cutting the tube to form the scaffold. This step would occur after the expanded tube is quenched. The subsequent, prolonged exposure to an elevated temperature, which may be included in the process, is intended to induce relaxation of internal stresses in the deformed precursor far more slowly than a typical annealing process. The process may be thought of as a "cold crystallization process".

Following is a discussion of a study conducted to determine a best or improved tube formation for use in making a peripherally-implanted polymer scaffold. Principally, the study was focused on determining what type of biaxially expanded tube might reduce a rate or number of strut fracturing and crack propagation for a peripherally-implanted scaffold, without adversely affecting other mechanical properties of the scaffold. Prior scaffolds have been formed from tubes having a biaxial expansion of between 400-450% (RE) and 20-45% (AE).

The processing parameters used to biaxially expand PLLA precursor tubes according to three different radial and axial expansion pairs are summarized in TABLE 1.

TABLE 1

| RE/AE | Expand Heat (F) | Air Flow (scfh) | Pre-heat Dwell (s) | Expand Heat Speed mm/s | Expand Pressure (psi) | Cool Time (s) | Initial OD (μm) | Initial ID (μm) | Final OD (μm) | Final ID (μm) |
|---|---|---|---|---|---|---|---|---|---|---|
| 400/200 | 240 | 53 | 35 | 0.45 | 180 | 30 | 100 | 50 | 275.6 | 262.8 |
| 200/200 | 240 | 53 | 35 | 0.45 | 180 | 30 | 190 | 50 | 275.6 | 262.8 |
| 400/45 | 235 | 53 | 40 | 0.45 | 110 | 30 | 139 | 51 | 275.6 | 251 |
| 480/45 | 240 | 53 | 46 | 0.45 | 130 | 30 | 319 | 51 | 275.6 | 251.8 |

In addition to the 400/200, 200/200 and 400/45 biaxial expansion case, the study considered a 480/45 biaxially expanded tube. The 400/45 case is the control case, representing one existing tube formation for scaffolds.

After tube formation according to TABLE 1, both tubes and scaffolds made from tubes were subjected to various tests to evaluate mechanical properties such as radial strength and elongation at break change as a function of different biaxial expansions. The tests conducted are summarized in TABLE 2 and described in more detail below:

TABLE 2

Figure 2:
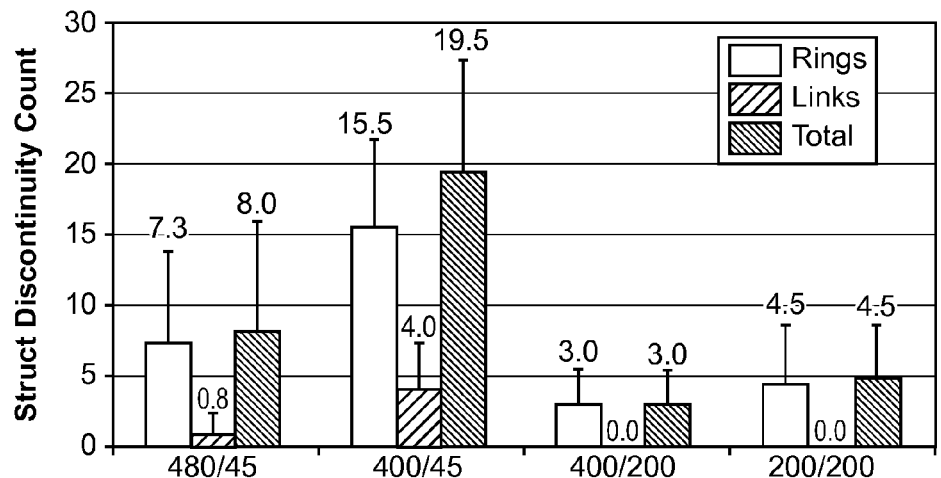
FIG. 2 is a plot showing the number of struts, links and total number of discontinuities for scaffolds made from tubes having different biaxial expansion ratios. The test is an axial fatigue test simulating six months of walking.
Figure 3:
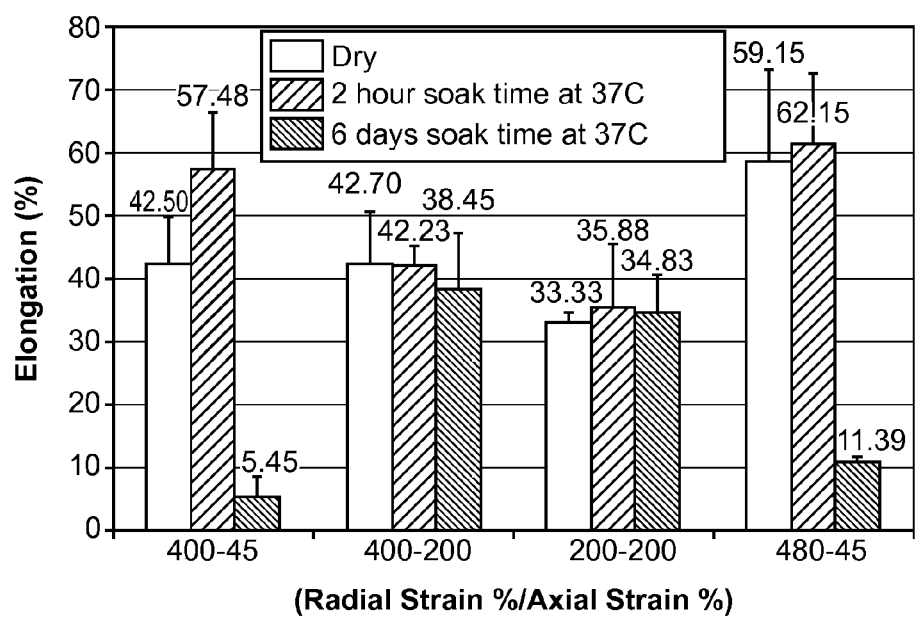
FIG. 3 is a plot show the axial elongation at break for the scaffolds formed from the tubes having the different biaxial expansion ratios. The elongation is shown for three cases: dry, 2 hour soak and 6 day soak in water at 37 Degrees C.
Figure 4:
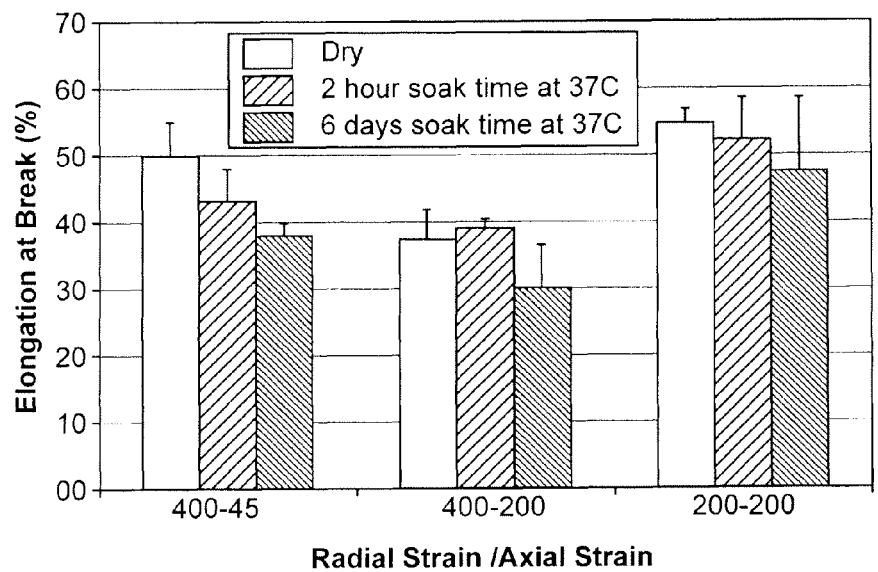
FIG. 4 is a plot show the radial elongation at break for the scaffolds formed from the tubes having the different biaxial expansion ratios. The elongation is shown for three cases: dry, 2 hour soak and 6 day soak in water at 37 Degrees C.
Figure 5:
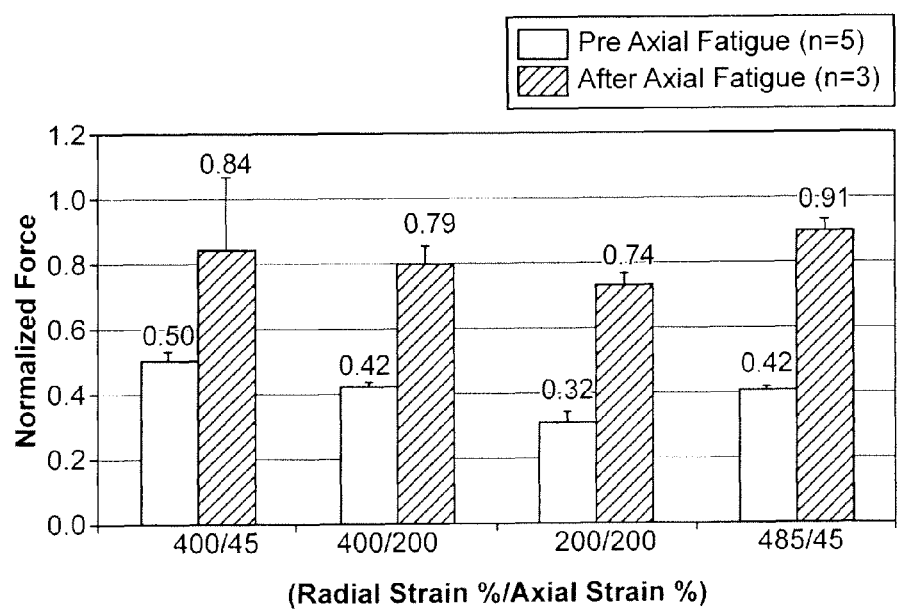
FIG. 5 is a plot show the normalized radial strength (N/mm) for the scaffolds formed from the tubes having the different biaxial expansion ratios. The radial strength is shown for scaffolds prior to, and after axial fatigue testing.
Figure 6:
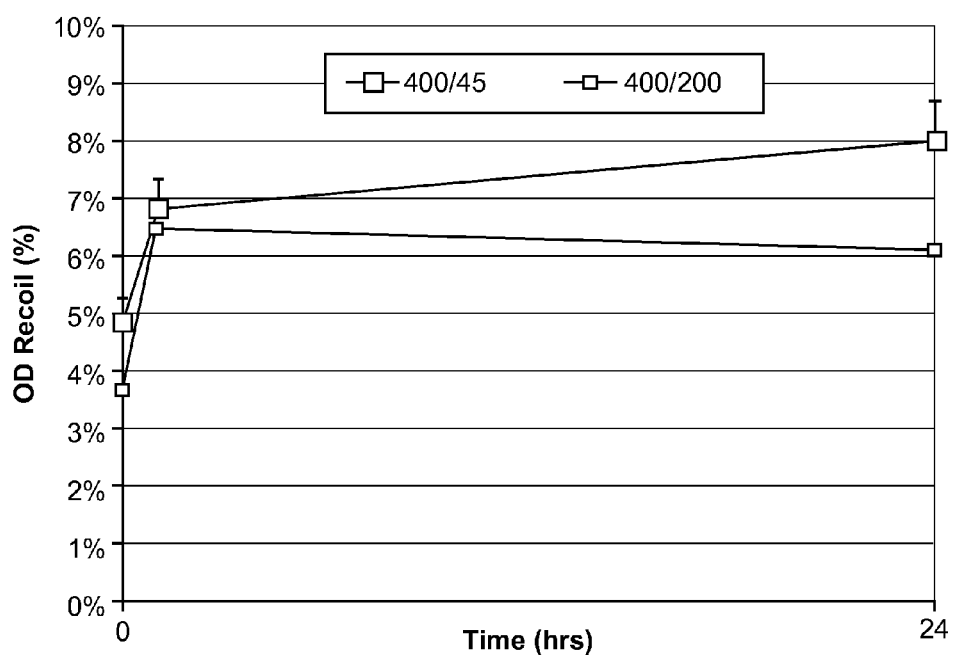
FIG. 6 is a plot showing 24 hour radial recoil for two of the scaffolds formed from the tubes having the different biaxial expansion ratios.

| Test | Type | Purpose | Test article | FIGURE |
|---|---|---|---|---|
| A | fatigue test (axial) | To compare number of fractured struts/links during 6 month axial fatigue for different biaxial expansions | V79 Scaffold | FIG. 2 |
| B | Elongation at break (axial) | To compare elastic property in axial direction for different soak times and different biaxial expansions | dog bone samples | FIG. 3 |
| C | Elongation at break (radial) | To compare elastic property in radial direction for different soak times and different biaxial expansions | dog bone samples | FIG. 4 |
| D | Radial strength and stiffness | To compare change in radial strength for different biaxial expansions and both post and pre axial fatigue scaffolds | V79 scaffold | FIG. 5 |
| E | Recoil | To compare changes in radial recoil for different biaxial expansions | V79 Scaffold | FIG. 6 and Table 4 |

For each test there are 3-5 samples used to generate statistics. The results of the tests are summarized in FIGS. 2-6 and below.

The V79 scaffold (described in FIGS. 7, 10B and 11B) has a 0.011 in wall thickness and 7 mm OD. The tubes, from which dog bone samples were made, had the same wall thickness and OD as the scaffolds. The scaffolds were prepared by crimping the scaffolds to a FoxSV™ 0.018 PTA catheter, which is available from Abbott Vascular, Inc. The 7.0 OD scaffolds were crimped to 2.03 mm OD according to the process described U.S. application Ser. No. 13/644,347.

The crimped scaffolds were E-beam sterilized and balloon expanded to a 5.4 mm OD according to normal balloon inflation protocol for the PTA catheter. For the tests a scaffold is deployed into a polycarbonate block of inner diameter 5.4 (OD of scaffold). For axial fatigue tests the scaffolds were deployed into a 5.0 mm ID tubing.

Test A simulates the axial loading environment on the peripherally scaffold when implanted in the femoral artery and subjected to these repeated loads caused by normal walking. It has been found that this type of loading is a major contributor to failure of scaffold struts. As such, it is believed a good benchmark for evaluating the fitness of a peripheral scaffold. It is estimated that about 1 million axial loading cycles represent one year of walking by the average person. For a scaffold according to preferred embodiments the time period of most interest is 6 months, which time period can be estimated by performing an accelerated axial cyclic loading over 6 days (500,000 cycles over the course of six days). Throughout the 6 day loading period the scaffold is submerged in water at a temperature of 37 Deg. C (body temperature). Mean and standard deviation values (n=5) from Test A are shown in FIG. 2.

For Tests B and C (material testing) ring and strip dog bone sample were cut from the biaxial expanded tubes using a laser, then E-beam sterilized (as a scaffold would be sterilized before being implanted). The dog bones were chosen to measure axial and circumferential properties of the biaxially-expanded material, for purposes of better understanding the behavior of the scaffold, e.g., when subjected to axial fatigue loading and changes due to hydration (as discussed below). For both Tests B and C elongation at break were measured at room temperature for three cases: dog bones submerged in water for 6 days at 37 Deg. C, dog bones submerged in water for 2 hours at 37 Deg. C, and dog bones not submerged in water.

For radial or circumferential elongation at break (Test B), the ring was cut from the 0.011 wall thickness and 7 OD tube and a narrowed section formed (using a laser) to measure elongation at break in the circumferential direction. The ring was subjected to a uniform radial outward load at a rate of 50 mm/min and the circumferential strain measured until break. Mean and standard deviation values (n=5) from Test B are shown in FIG. 3.

For the axial elongation at break test (Test C), a strip was cut from the tube (using the laser) and a narrowed section formed in the strip to measure axial elongation at break. The strip was subjected to an axial tensile load at a rate of 50 mm/min and the axial strain measured until break. Mean and standard deviation values (n=5) from Test C are shown in FIG. 4.

Test D estimates the radial strength and stiffness of the scaffold for two cases: a scaffold prior to, and after the axial fatigue test (Test A). Test D applies a uniform radial-inward force on the scaffold using an MSI RX550 Radial Force Tester and according to the test method/procedure under STM 2076919. Scaffolds not previously subjected to Test A were tested for radial strength. Also tested were scaffolds previously subjected to the axial fatigue loading, to evaluate the change in radial strength and stiffness after repeated fatigue loading in the axial direction. For 500,000 cycles, at the frequency of 1 Hz, the duration of Test A was 6 days, therefore the change in radial strength post soaking in water at 37 Deg. C was also observed from this same test of post axial-fatigue evaluation of radial strength.

Scaffolds previously subjected to Test A were re-soaked for 2 min in 37 Deg. C prior to being tested. Referring to FIG. 5, the force is referred to as "normalized" force, meaning a force normalized as to the length of the scaffold. Hence, the units are force per unit length or, in the case of FIG. 5 N/mm. The post-axial fatigue scaffolds used for this test were scaffolds having substantially intact rings. During fatigue testing water plasticizes the scaffolds, thereby allowing morphological changes especially in the amorphous phase of the material, and as a result radial strength and stiffness increases in spite of generated scaffold fractures.

Test E measures the recoil from the expanded diameter of 5.4 mm. A comparison between the 400/200 and 400/45 biaxially expanded scaffold recoils over a 24 hour period (n=3) is shown in FIG. 6. TABLE 3, below, shows mean and standard deviation for recoil after ½ hour (acute recoil), 1 hour, 1 day and 7 days. For these recoil measurements the scaffold is submerged in water at 37 Deg. C.

FIG. 2, showing the number of fractures in struts and links for scaffolds subjected to Test A (axial fatigue), indicates that a biaxial expansion of 400/200 or 200/200 will produce the fewest failures in the scaffold. Moreover, the tests reveal for the 400/200 and 200/200 scaffolds a statistically-significant lower number of discontinuous struts than the 400/45 and 480/45 cases, despite there being no failed linking elements.

This result suggests that a more balanced RE and AE may be beneficial for ring integrity, because despite there being no failed links, which axially interconnect rings formed by struts, for the 400/200 and 200/200 scaffolds the total number of struts that failed was less than in the cases where more links failed. The reasoning for choosing a more balanced biaxial expansion, in response to axial fatigue, is as follows. One might have surmised that if a link fails then there is less overall stress on a ring element since a load path to the ring has been severed. Thus, one might conclude that fewer struts should ultimately fail if more links fail. FIG. 2, however, suggests that a more balanced RE and AE, e.g., 400/200 or 200/200, will produce a better result despite the load paths to the struts being intact, i.e., no links fail.

FIG. 5 shows the normalized radial strength (force/length) for pre and post axial fatigue scaffolds (Test D). The results show that for scaffolds having substantially intact rings the radial force is higher for post-axial-fatigued-scaffolds than pre-axial-fatigued-scaffolds. Without wishing to be tied to any particular theory, we believe the effects on morphology are due at least in-part to water absorption. The material plasticizes when it hydrates, leading to increased chain mobility and as a result morphological changes, such as the degree of crystallinity and chain rearrangement in both the amorphous and at the interface of amorphous-crystalline phases influencing crystallite orientation. These changes can increase the scaffold's radial strength. The hydration process and resulting morphological changes can also cause relatively high circumferentially oriented scaffold (e.g., 400/45) to become less tough under a radial loading condition, but there is believed less change in the toughness of the bi-axial tubing for lower ratios of RE to AE (e.g., 400/200). Elongation at break is a good indicator of toughness for a polymer. Indeed, with regard to polymers suitable for use as a scaffold backbone, in many cases a higher elongation at break also indicates an increase in toughness.

Notably, in FIG. 5 there is little difference between the radial strength for scaffolds having 400/45 and 480/45 and scaffolds having a 400/200 biaxial expansion. One would have expected, instead, that the difference would be greater since the orientation of the crystalline structures/polymer chains in the 400/45 is far more than for 400/200. For both the pre and post axial fatigue the radial strength for scaffolds having the 400/200 biaxial expansion are about the same as in the scaffolds having the 400/45 and 480/45 biaxial expansion. FIG. 5 indicates that a more balanced radial and axial expansion does not have negative effects on radial strength (or stiffness) as one might have previously concluded.

Test E (FIG. 6 and TABLE 3) measures recoil of the scaffold for different biaxial expansions. The results indicate that a more balanced biaxial expansion can produce both a lower recoil after 7 days and earlier converge of the recoil.

TABLE 3

| RE/AE | Acute Recoil | 1 hour | 1 day | 7 days |
| --- | --- | --- | --- | --- |
| 400/45 | 4.9% ± 0.4% | 6.9% ± 0.5% | 8.1% ± 0.7% | 7.6% ± 0.4% |
| 480/45 | 3.6% ± 0.6% | 7.0% ± 1.4% | 8.1% ± 0.5% | 6.2% ± 1.2% |
| 400/200 | 3.7% ± 0.2% | 6.5% ± 0.6% | 6.2% ± 0.4% | 5.7% ± 1.2% |
| 200/200 | 4.5% ± 0.9% | 8.1% ± 0.3% | 8.0% ± 0.7% | 7.3% ± 1.2% |

As TABLE 3 indicates for 400/200 there is both an earlier convergence and monotonically decreasing recoil after 1 hour. The trend after one day (compared to 400/45) is shown in FIG. 6. Thus, the recoil is less and converges quicker for a more balanced biaxial expansion.

Tests B and C, as indicated earlier, are material tests using dog bones. FIG. 4 shows the radial or circumferential elongation at break for dry, 2 hour soaked, and 6 day soaked dog bone samples. Here there is a general decrease in the radial elongation at break.

FIG. 3 shows the axial elongation at break for dry, 2 hour soaked, and 6 days soaked dog bone samples. For the dry and 2 hour soak times the elongation at break either stays the same or decreases slightly for each case. Similar measurements for dry, 2 hour and 6 day material modulus/stiffness show a decrease the longer the material is submerged in water.

However, after 6 days soaking in 37 C water the elongation at break drops dramatically for the 400/45 and 480/45 cases. Since it was found that both the modulus and elongation at break drops with increased hydration, the material's toughness (or strain energy required to break the material) drops significantly for the hydrated and less balanced biaxial expansion cases. When the 400/45 and 480/45 dog bones are tested their ultimate strain in the axial direction decreases dramatically.

As discussed earlier, we believe the results can be explained by morphological changes in the polymer material due to the water hydration/plasticizing effect. With 200% axial strain, the changes in that direction post hydration is less dramatic compared to the 45% axial strain case. In the 400/45 case most polymer chains have a nearly circumferential orientation meaning that the axial cohesive strength is mainly provided by inter-molecular forces. These inter-molecular forces, which hold the material together, are substantially weakened as Tg decreases (as a result of material getting plasticized in wet condition and implanted at an elevated temperature), thereby allowing more chain motion as the entropy and the free volume is increased. In the 400/200 case, more axial cohesive strength is provided by the polymer chain backbone. This morphology creates potential for physical crosslinks by close packing of chains, strain-induced additional crystallinity, and axial orientation of the crystal structure. When wet, chains may lose some of their orientation during the early hydration process, but the yield strain is not much affected as the chains need to slip a long distance before the material yields.

In the axial direction the main cohesive strength is provided by the polymer chain backbone, which are oriented more in the axial direction and create the potential for physical crosslinks by close packing of chains, strain-induced additional crystallinity, and axial orientation of the crystal structure. When wet, a loss of orientation in the axial direction will result in a drop of yield strain and modulus in the axial direction.

Modulus data from the material testing show components in the radial and axial direction. The crowns of a scaffold (high stress regions during radial loading) are orientated at a certain angle where both an axial and radial component directions for polymer chains can contribute to the stiffness behavior. The reported stiffness was tested on a scaffold compressed circumferentially. In the material axial fatigue testing the scaffold is loading in the axial direction, which provides the load path through the links to the rings, along the longitudinal axis. For the radial compression case, the axial expansion may play a more significant role in the results than the radial expansion did in the axial fatigue results.

The above test results indicate that a more balanced biaxial expansion, e.g., 400/200 or 200/200 tend to benefit the scaffold's resistance to fracture in both radial and axial directions, reduce the recoil and/or cause recoil to converge to steady state in less time, and has a less dramatic change in material strength properties after being implanted into a peripheral vessel.

Based on this testing, it was concluded that by choosing an optimal combination of a balanced biaxial expansion, a peripheral scaffold's fitness for use in the peripheral vessel improves. TABLE 4 summarizes results from the testing of the 480/45, 400/45, 400/200 and 200/200 biaxial expansion cases and compares the radial and axial elongation at break.

TABLE 4

| Expansion Ratios (RE/AE) | | (radial elongation at break)/ (axial elongation at break) | |
|---|---|---|---|
| 480/45 | 10.7 | — | — |
| 400/45 | 8.9 | 38/5.5 | 6.9 |
| 400/200 | 2 | 31/38 | 0.82 |
| 200/200 | 1 | 48/35 | 1.37 |

The ratio of axial to radial elongation at break ratio is a measure of the overall intensity of distortion (change in shape). A higher ratio means greater distortion between axial and radial loading.

Using this criterion, it is believed that the 400/200 case provided the best overall mechanical properties suited for the peripheral scaffold environment. Based on the test data, the following conclusions were reached in regard to material or processing properties of a tube that can provide an improved peripheral scaffold product. In the embodiments, the biaxial expansion may range from about 400-500 in the radial direction and from about 150-200 in the axial direction. In the embodiments, the ratio RE/AE may be between about 2 and 1, 2.5 to 1, 3 to 1, and 4 to 1.

Following is a description of preferred embodiments of a scaffold made from a tube constructed in accordance with the disclosure.

Figure 8:
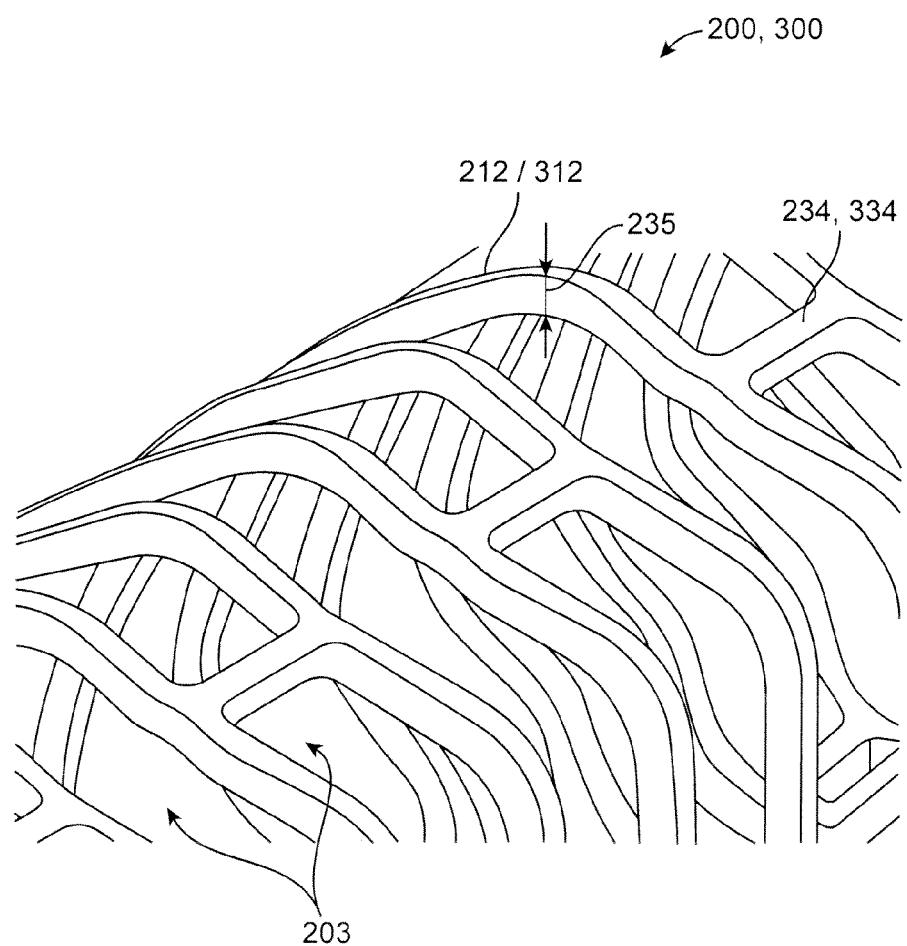
FIG. 8 is a partial perspective view of a scaffold structure.

The strengthened and toughened cylindrical, polymer tube of FIG. 1 is formed into a scaffold structure, in one embodiment a structure having a plurality of struts 230 and links 234 forming a pattern 200 as shown in FIG. 7 (pattern 200 is illustrated in a planar or flattened view), which is about the pattern for the scaffold before crimping and after the scaffold is plastically, or irreversibly deformed from its crimped state to its deployed state within a vessel by balloon expansion. The pattern 200 of FIG. 7, therefore, represents a tubular scaffold structure (as partially shown in three dimensional space in FIG. 8), so that an axis A-A is parallel to the central or longitudinal axis of the scaffold. FIG. 8 shows the scaffold in a state prior to crimping or after deployment. As can be seen from FIG. 8, the scaffold comprises a framework of struts and links that define a generally tubular body. The cylindrical, deformed tube of FIG. 1 may be formed into this open framework of struts and links described in FIGS. 7-8 by a laser cutting device, preferably, a pico-second green light laser that uses Helium gas as a coolant during cutting.

Referring to FIG. 7, the pattern 200 includes longitudinally-spaced rings 212 formed by struts 230. There are eight crests formed by the struts. A ring 212 is connected to an adjacent ring by no more than two links 234, each of which extends parallel to axis A-A. In this first embodiment of a scaffold pattern (pattern 200) two links 234 connect the interior ring 212, which refers to a ring having a ring to its left and right in FIG. 7, to each of the two adjacent rings. Thus, ring 212b is connected by two links 234 to ring 212c and two links 234 to ring 212a. An end ring (not shown) is an end ring connected to only one other ring.

A ring 212 is formed by struts 230 connected at crowns 207, 209 and 210. A link 234 is joined with struts 230 at a crown 209 (W-crown) and at a crown 210 (Y-crown). A crown 207 (free-crown, U-crown or unsupported crown) does not have a link 234 connected to it. Preferably the struts 230 that extend from a crown 207, 209 and 210 extend at a constant angle from a crown center, i.e., the rings 212 are approximately zig-zag in shape, as opposed to sinusoidal for pattern 200. As such, in this embodiment a ring 212 height, which is the longitudinal distance between adjacent crowns 207 and 209/210 may be derived from the lengths of the two struts 230 connecting at the crown and a crown angle e. In some embodiments the angle e at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 7). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than, or equal to a maximum expanded scaffold diameter that the delivery balloon can, or is capable of producing when inflated.

A second embodiment of a scaffold structure has the pattern 300 illustrated in FIG. 9. Like the pattern 200, the pattern 300 includes longitudinally-spaced rings 312 formed by struts 330. There are twelve crests formed by the struts for each ring 312. A ring 312 is connected to an adjacent ring by no more than two links 334, each of which extends parallel to axis A-A. The description of the structure associated with rings 212, struts 230, links 234, and crowns 207, 209, 210 in connection with FIG. 7, above, also applies to the respective rings 312, struts 330, links 334 and crowns 307, 309 and 310 of the second embodiment, except that in the second embodiment there are 12, as opposed to 8 crests for each ring 312 for pattern 300.

Figure 10A:
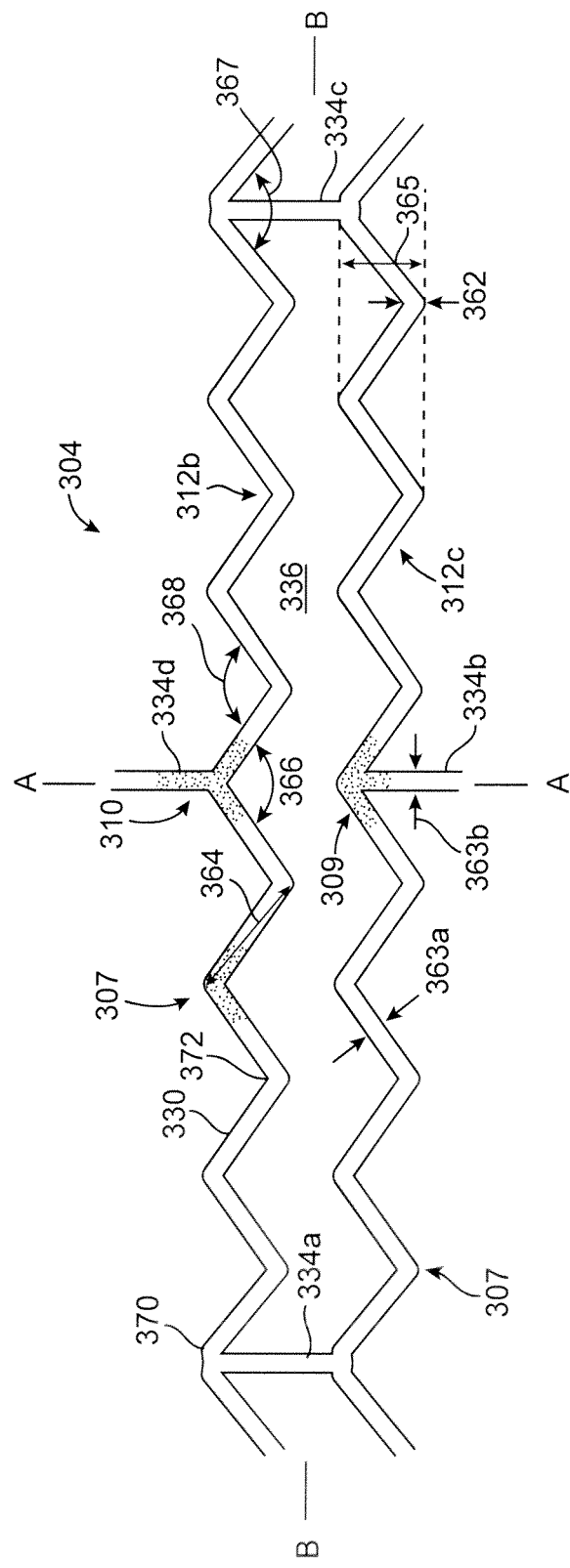
FIG. 10A is a planar view of a portion of the scaffold pattern of FIG. 9 taken at section VA-VA.
Figure 10B:
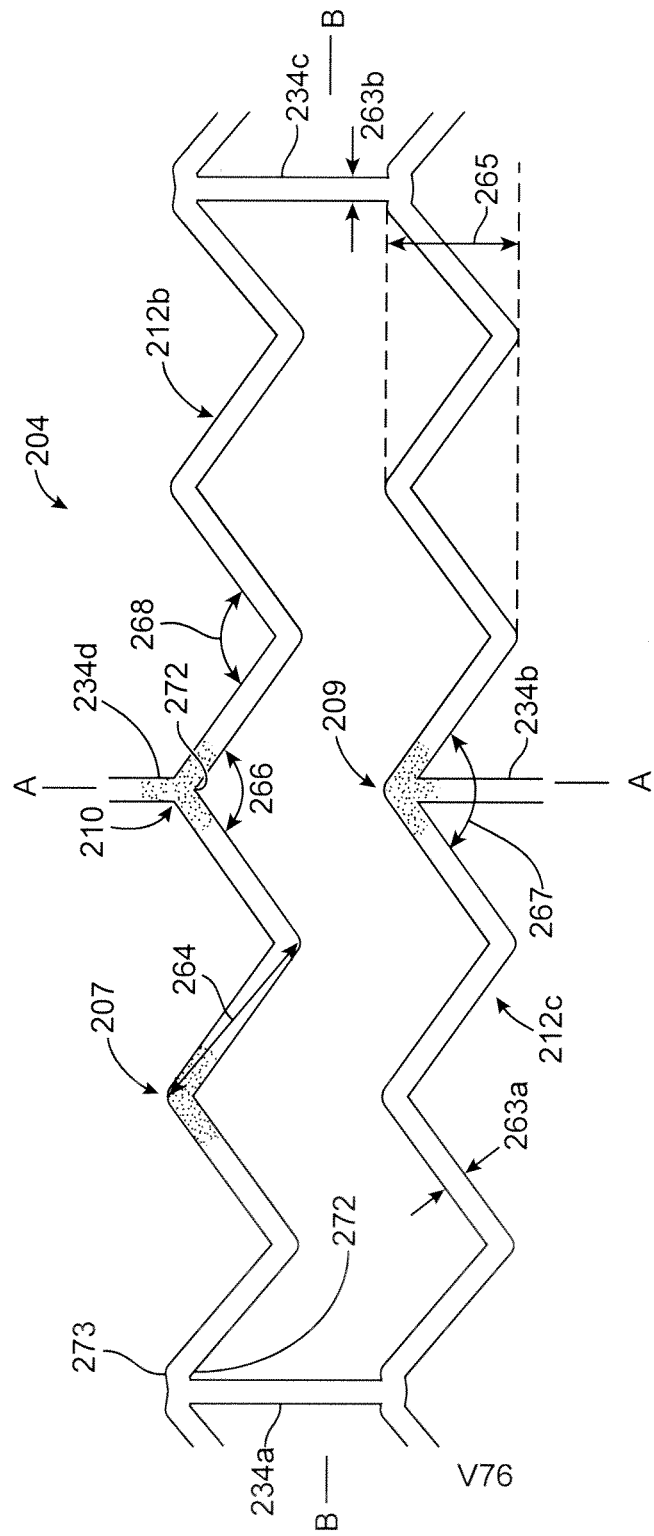
FIG. 10B is a planar view of a portion of the scaffold pattern of FIG. 7 taken at section VB-VB.

FIGS. 10A and 10B depict aspects of the repeating pattern of closed cell elements associated with each of the patterns 300 and 200, respectively. FIG. 10A shows the portion of pattern 300 bounded by the phantom box VA and FIG. 10B shows the portion of pattern 200 bounded by the phantom box VB. Therein are shown cell 304 and cell 204, respectively. In FIGS. 10A, 10B the vertical axis reference is indicated by the axis B-B and the longitudinal axis A-A. There are two such cells 204 formed by each pair of rings 212 in pattern 200, e.g., two cells 204 are formed by rings 212b and 212c and the links 234 connecting this ring pair, another two cells 204 are formed by rings 212a and 212b and the links connecting this ring pair, etc. Similarly, there are two cells 304 formed by rings 312b and 312c and the links 334 connecting this ring pair, another two cells 304 are formed by rings 312a and 312b and the links connecting this ring pair, etc.

Referring to FIG. 10A, the space 336 of cell 304 is bounded by the longitudinally spaced rings 312b and 312c portions shown, and the circumferentially spaced and parallel links 334a and 334c connecting rings 312b and 312c. Links 334b and 334d extend parallel to each other and connect the cell 304 to the right and left adjacent ring in FIG. 9, respectively. Link 334b connects to cell 304 at a W-crown 309. Link 334d connects to cell 304 at a Y-crown 310. A "W-crown" refers to a crown where the angle extending between a strut 330 and the link 336 at the crown 310 is an acute angle (less than 90 degrees). A "Y-crown" refers to a crown where the angle extending between a strut 330 and the link 334 at the crown 309 is an obtuse angle (greater than 90 degrees). The same definitions for Y-crown and W-crown also apply to the cell 204. There are 20 unconnected or "U-crowns" 307 for cell 304, which may be understood as 20 crowns devoid of a link 334 connected at the crown. There are always 5 U-crowns between a Y-crown or W-crown for the cell 304.

Additional aspects of the cell 304 of FIG. 10A include angles for the respective crowns 307, 309 and 310. Those angles are identified in FIG. 11A. For the scaffold having the pattern 300 the struts 330 have strut widths 363 and strut lengths 364, and the links 334 have link widths 363. Each of the rings 312 has a ring height 365. The radii at the crowns are, in general, not equal to each other. The radii of the crowns are identified in FIG. 11A. Cell 304 of pattern 300 may be regarded as a symmetric cell, by virtue of it always having two U-crowns on each side of a W-crown and Y-crown as shown.

Referring to FIG. 10B, the space 236 of cell 204 is bounded by the portions of longitudinally spaced rings 212b and 212c as shown, and the circumferentially spaced and parallel links 234a and 234c connecting these rings. Links 234b and 234d connect the cell 204 to the right and left adjacent rings in FIG. 7, respectively. Link 234b connects to cell 236 at a W-crown 209. Link 234d connects to cell 236 at a Y-crown 210. There are 12 U-crowns 207 for cell 204, which may be understood as 12 crowns devoid of a link 234 connected at the crown. Cell 204 may also be regarded as a symmetric cell, by virtue of it always having 3 U-crowns on each side of a W-crown and Y-crown as shown.

Additional aspects of the cell 204 of FIG. 10B include angles for the respective crowns 207, 209 and 210. Those angles are identified in FIG. 10B as angles 267, 269 and 268, respectively associated with crowns 207, 209 and 210. For the scaffold having the pattern 200 the struts 230 have strut widths 263a and strut lengths 264, the crowns 207, 209, 210 have crown widths 270, and the links 234 have link widths 263b. Each of the rings 212 has a ring height 265. The radii of the crowns are identified in FIG. 10A as inner radii 272 and outer radii 273.

The V79 and V80 both have a symmetric cell design. A "symmetric" cell design (as shown in FIGS. 10A and 10B) has an equal number of U-crowns on each side of a W-crown or Y-crown. An example of an asymmetric cell design would be the V23 scaffold pattern, as described in US2011/0190871.

A significant difference between the V80 and V79 is that the V79 (as well as other designs, described below) has eight crests and two links whereas the V80 design has twelve crests and two links. Having more crests and therefore shorter bar arms than other designs, the V80 has a higher density of struts. For example, a 60 mm V80 scaffold has 33 rings and a total of 396 ring struts/scaffold, which can be compared to a total of 216 ring struts (27 rings×8 struts per ring)/scaffold for the V79 design, and 200 ring struts/scaffold for the V59. In-vivo tests show that with a higher density of struts there is a lower late lumen loss for the V80.

Crimping of the scaffold, as detailed in U.S. application Ser. No. 13/194,162, includes heating the polymer material to a temperature less then, but near to the glass transition temperature of the polymer. In one embodiment the temperature of the scaffold during crimping is raised to about 5 to 10 degrees below the glass transition temperature for PLLA. When crimped to the final, crimped diameter, the crimping jaws are held at the final crimp diameter for final dwell period. This method for crimping a polymer scaffold having crush recovery is advantageous to reduce recoil when the crimp jaws are released. After the final dwell period, the scaffold is removed from the crimper and a constraining

What is claimed is:

1. A method, comprising:
   biaxially expanding a polymer tube according to a radial expansion (RE) and axial expansion (AE) wherein the ratio RE/AE is between 400/200 and 200/200, and
   forming the scaffold from the biaxially-expanded tube, including forming a network of rings interconnected by links, wherein the scaffold has a pre-crimp diameter,
   wherein the scaffold is configured for being plastically deformed when crimped to a balloon and plastically deformed when expanded by the balloon, and wherein the scaffold attains at least 80% of the pre-crimp diameter after being crushed to 70% of the pre-crimp diameter, and
   wherein the scaffold exhibits a monotonically decreasing radial recoil after one hour from being plastically deformed to an expanded state by the balloon.

2. The method of claim 1,
   wherein the scaffold forming a network of rings interconnected by links includes 8 or 12, or between 8 and 12 crests per ring, and
   at most 2 links connecting adjacent rings,
   wherein each end of a link is connected to a crest of a ring and there are an equal number of unsupported crests on each side of the crest connected to the link.

3. The method of claim 2, wherein the scaffold has between a 5 and 7 mm outer diameter and between 0.008 and 0.012 in wall thickness.

4. The method of claim 1, wherein the scaffold has a pre-crimp diameter of greater than 5 mm and a wall thickness of between 0.008 in and 0.012 in.

5. The method of claim 1,
   wherein material of the biaxially-expanded tube has a ratio of a radial elongation at break and axial elongation at break of less than 1, and
   the network of rings interconnected by links includes
   8 to 12 crests per ring,
   a plurality of U crowns, Y crowns and W crowns at each ring,
   the rings include a first ring, a second ring adjacent the first ring, a third ring adjacent the second ring, and a fourth ring adjacent the third ring,
   the first ring is connected to the second ring by at most two links, each of which being connected to the first ring at a W crown and the second ring at a Y crown and such that there are an equal number of U crowns on each side of a W crown of the first ring and each side of a Y crown of the second ring,
   the second ring is connected to the third ring by at most two links, each of which being connected to the second ring at a W crown and the third ring at a Y crown and such that there are an equal number of U crowns on each side of a W crown of the second ring and each side of a Y crown of the third ring,
   the third ring is connected to the fourth ring by at most two links, each of which being connected to the third ring at a W crown and the fourth ring at a Y crown and such that there are an equal number of U crowns on each side of a W crown of the third ring and each side of a Y crown of the fourth ring, and
   each of the links has a longitudinal axis and extends parallel to the longitudinal axis of the scaffold, and wherein each of the links connecting the first ring to the second ring is co-linear with a respective one of the links connecting the third ring to the fourth ring.

6. The method of claim 1, wherein the scaffold exhibits a radial recoil 7 days from being plastically deformed to an expanded state that is less than the radial recoil after 1 day from being plastically deformed to an expanded state.

7. The method of claim 1, wherein the scaffold normalized radial strength is about 0.79 N/mm.

8. The method of claim 1, wherein the scaffold has a crystallinity below 50%.

9. The method of claim 1, wherein the tube material is poly(L-lactide).

10. The method of claim 1, wherein the scaffold includes crowns formed on rings, wherein a crown angle is 81 degrees.

11. A method, comprising:
    biaxially expanding a tube, wherein an amount of radial verses axial expansion of the tube is such that a ratio of an elongation at break in the radial direction and an elongation at break in the axial direction of the biaxially-expanded tube material is equal to, or less than 1.1; and
    forming a scaffold from the biaxially-expanded tube, including forming a network of rings interconnected by links;
    wherein the formed scaffold has a pre-crimp diameter, wherein the scaffold is configured for being plastically deformed when crimped to a balloon and plastically deformed when expanded by the balloon, and wherein the scaffold attains at least 80% of the pre-crimp diameter after being crushed to 70% of the pre-crimp diameter.

12. The method of claim 11, wherein the network of rings interconnected by links includes
    a plurality of U crowns, Y crowns and W crowns at each ring,
    the rings include a first ring, a second ring adjacent the first ring, a third ring adjacent the second ring, and a fourth ring adjacent the third ring,
    the first ring is connected to the second ring by at most two links, each of which being connected to the first ring at a W crown and the second ring at a Y crown and such that there are an equal number of U crowns on each side of a W crown of the first ring and each side of a Y crown of the second ring,
    the second ring is connected to the third ring by at most two links, each of which being connected to the second ring at a W crown and the third ring at a Y crown and such that there are an equal number of U crowns on each side of a W crown of the second ring and each side of a Y crown of the third ring,
    the third ring is connected to the fourth ring by at most two links, each of which being connected to the third ring at a W crown and the fourth ring at a Y crown and such that there are an equal number of U crowns on each side of a W crown of the third ring and each side of a Y crown of the fourth ring, and
    each of the links has a longitudinal axis and extends parallel to the longitudinal axis of the scaffold, and wherein each of the links connecting the first ring to the second ring is co-linear with a respective one of the links connecting the third ring to the fourth ring.

13. The method of claim 12, wherein the scaffold has a pre-crimp diameter of greater than 5 mm and a wall thickness of between 0.008 in and 0.012 in.

14. The method of claim 11, wherein each end of one of the links forms with one of the rings a W or Y crown and there are an equal number of U crowns on each side of the Y or W crown.

15. The method of claim 11, wherein the scaffold has between a 5 and 7 mm outer diameter and between 0.008 and 0.012 in wall thickness.

16. The method of claim 11, wherein a ring has 12 crests and a pair of rings is adjoined by at most 2 links.

17. The method of claim 11, wherein the tube is biaxially expanded according to a radical expansion (RE) and axial expansion (AE), and wherein the ratio RE/AE is 2:1, 2.5:1, 3:1 or 4:1.

18. A method, comprising:
biaxially expanding a tube, wherein an amount of radial verses axial expansion of the tube is such that a ratio of an elongation at break in the radial direction and an elongation at break in the axial direction of the biaxially-expanded tube material is equal to, or less than 1.1; and forming a scaffold from the biaxially-expanded tube, including forming a network of rings interconnected by links, wherein the formed scaffold has a pre-crimp diameter, wherein the scaffold is configured for being plastically deformed when crimped to a balloon and plastically deformed when expanded by the balloon, and wherein the scaffold attains at least 80% of the pre-crimp diameter after being crushed to 70% of the pre-crimp diameter; and crimping the scaffold to the balloon, wherein the pre-crimp diameter is between 1 and 1.5 times greater than an expanded diameter for the balloon.

19. The method of claim 18, wherein the tube is biaxially expanded according to a radial expansion (RE) and axial expansion (AE), and wherein the ratio RE/AE is 2:1, 2.5:1, 3:1 or 4:1.

* * * * *